US010576280B2

(12) United States Patent
Claude et al.

(10) Patent No.: US 10,576,280 B2
(45) Date of Patent: Mar. 3, 2020

(54) TREATMENT DEVICE INCLUDING WIRELESS INTERFACE AND USER APPLICATION

(71) Applicant: TIVIC HEALTH SYSTEMS INC., Menlo Park, CA (US)

(72) Inventors: John Claude, Redwood City, CA (US); Christopher A. Wiklof, Everett, WA (US); Jennifer Ernst, Union City, CA (US); Blake Gurfein, Oakland, CA (US)

(73) Assignee: TIVIC HEALTH SYSTEMS INC., Menlo Park, CA (US)

( * ) Notice: Subject to any disclaimer, the term of this patent is extended or adjusted under 35 U.S.C. 154(b) by 0 days.

(21) Appl. No.: 16/280,412

(22) Filed: Feb. 20, 2019

(65) Prior Publication Data

US 2019/0217094 A1    Jul. 18, 2019

Related U.S. Application Data

(63) Continuation of application No. PCT/US2018/051385, filed on Sep. 17, 2018.
(Continued)

(51) Int. Cl.
*A61N 1/36* (2006.01)
*A61B 5/053* (2006.01)
(Continued)

(52) U.S. Cl.
CPC .......... *A61N 1/36031* (2017.08); *A61B 5/053* (2013.01); *A61N 1/02* (2013.01);
(Continued)

(58) Field of Classification Search
CPC .............. A61N 1/3787; A61N 1/36014; A61N 1/0546; A61N 1/3925; A61N 1/36146;
(Continued)

(56) References Cited

U.S. PATENT DOCUMENTS

| 4,926,880 A | 5/1990 | Claude et al. |
| 5,772,605 A | 6/1998 | Weijand |

(Continued)

FOREIGN PATENT DOCUMENTS

| JP | 2006-000567 | 1/2006 |
| KR | 20-0389849 | 7/2005 |

(Continued)

OTHER PUBLICATIONS

PCT International Search Report and Written Opinion dated Jan. 14, 2019, for PCT International Patent Application No. PCT/US2018/051385 filed Sep. 17, 2018, 18 pages.

*Primary Examiner* — Deborah L Malamud
(74) *Attorney, Agent, or Firm* — Christopher A. Wiklof; Nicholas S. Bromer; Launchpad IP, Inc.

(57) ABSTRACT

A handheld sinus treatment device provides sinus relief treatment to a user. The handheld sinus treatment device includes a wireless receiver configured to receive wireless signals including control data from a handheld electronic device. The user positions a treatment electrode of the sinus treatment device at a treatment location on the user's face corresponding to a sinus nerve node. The sinus treatment device provides electrical sinus treatment stimulation in accordance with the control data.

19 Claims, 12 Drawing Sheets

Related U.S. Application Data

(60) Provisional application No. 62/559,792, filed on Sep. 18, 2017, provisional application No. 62/560,120, filed on Sep. 18, 2017, provisional application No. 62/491,793, filed on Apr. 28, 2017.

(51) Int. Cl.
| | | |
|---|---|---|
| *A61N 1/04* | (2006.01) | |
| *A61N 1/02* | (2006.01) | |
| *A61N 1/20* | (2006.01) | |
| *A61B 5/00* | (2006.01) | |
| *A61B 18/14* | (2006.01) | |
| *A61N 1/32* | (2006.01) | |

(52) U.S. Cl.
CPC .............. *A61N 1/04* (2013.01); *A61N 1/0428* (2013.01); *A61N 1/0456* (2013.01); *A61N 1/0472* (2013.01); *A61N 1/205* (2013.01); *A61N 1/36* (2013.01); *A61N 1/3601* (2013.01); *A61N 1/36014* (2013.01); *A61N 1/36021* (2013.01); *A61B 5/6814* (2013.01); *A61B 5/7225* (2013.01); *A61B 18/14* (2013.01); *A61N 1/326* (2013.01); *A61N 1/3603* (2017.08)

(58) Field of Classification Search
CPC ...... A61N 1/0472; A61N 1/08; A61N 1/0526; A61B 5/4836; A61B 5/0028; A61B 5/04; A61B 5/0404; A61B 5/0482; A61B 5/0484; A61B 5/486; A61B 5/6801; A61B 5/6803; A61B 5/6867; H04B 13/005

See application file for complete search history.

(56) References Cited

U.S. PATENT DOCUMENTS

| | | | |
|---|---|---|---|
| 6,109,268 | A | 8/2000 | Thapliyal et al. |
| 8,630,714 | B1 | 1/2014 | Webb |
| 8,996,137 | B2 * | 3/2015 | Ackermann ....... A61N 1/36046 607/135 |
| 9,002,479 | B1 | 4/2015 | Unarce, Jr. |
| 9,630,003 | B2 | 4/2017 | Thompson et al. |
| 10,155,108 | B2 | 12/2018 | Ackermann et al. |
| 10,252,048 | B2 | 4/2019 | Loudin et al. |
| 2004/0044390 | A1 | 3/2004 | Szeles |
| 2007/0293918 | A1 | 12/2007 | Thompson et al. |
| 2009/0030476 | A1 | 1/2009 | Hargrove |
| 2011/0276107 | A1 | 11/2011 | Simon et al. |
| 2013/0085551 | A1 | 4/2013 | Bachinski et al. |
| 2014/0296934 | A1 | 10/2014 | Gozani et al. |

FOREIGN PATENT DOCUMENTS

| | | |
|---|---|---|
| KR | 20-0414456 | 4/2006 |
| KR | 10-1534525 | 7/2015 |
| KR | 10-20150110935 | 10/2015 |

\* cited by examiner

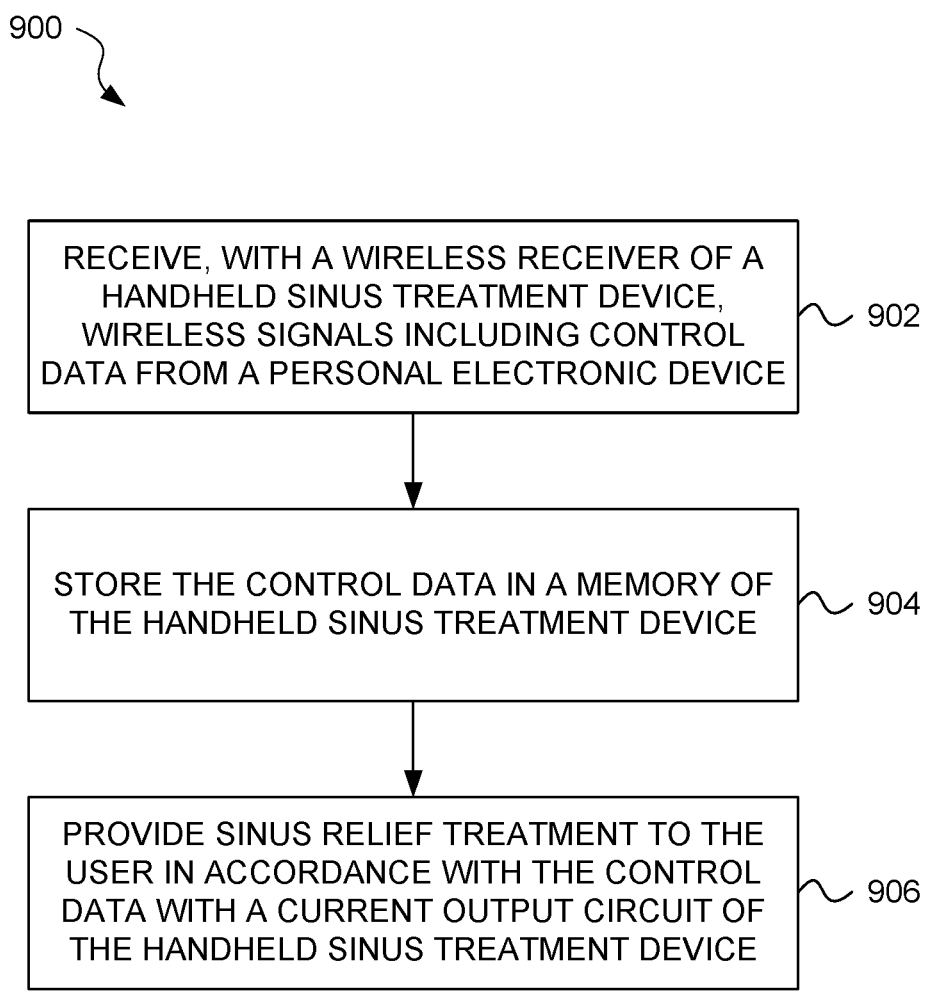

TREATMENT DEVICE INCLUDING WIRELESS INTERFACE AND USER APPLICATION

CROSS REFERENCE TO RELATED APPLICATIONS

The present application is a Continuation Application of co-pending International PCT Patent Application No. PCT/US2018/051385, entitled "TREATMENT DEVICE INCLUDING WIRELESS INTERFACE AND USER APPLICATION," filed Sep. 17, 2018. International PCT Patent Application No. PCT/US2018/051385 claims priority benefit from U.S. Provisional Patent Application No. 62/559,792, entitled "TREATMENT DEVICE INCLUDING WIRELESS INTERFACE AND USER APPLICATION," filed Sep. 18, 2017. International PCT Patent Application No. PCT/US2018/051385 also claims priority benefit from U.S. Provisional Patent Application No. 62/491,793, entitled "SINUS DEVICE WITH ADAPTIVE CIRCUIT," filed Apr. 28, 2017. International PCT Patent Application No. PCT/US2018/051385 also claims priority benefit from U.S. Provisional Patent Application No. 62/560,120, entitled "ADAPTIVE TRIGGER FOR A MICROCURRENT STIMULATION DEVICE," filed Sep. 18, 2017. Each of these patent applications, to the extent not inconsistent with the disclosure herein, is incorporated by reference.

SUMMARY

According to an embodiment, a handheld sinus treatment device includes a memory, a current output circuit including a treatment electrode configured to provide sinus relief treatment stimulation to a user, a wireless receiver configured to receive wireless signals including control data from a personal electronic device, and a microcontroller operably coupled to the memory and the wireless receiver. The microcontroller is configured to receive the control data via the wireless receiver, write the control data to the memory, and cause the current output circuit to provide sinus relief treatment stimulation to the user in accordance with the control data.

According to an embodiment, a method for operating a handheld sinus treatment device includes receiving, with a wireless receiver of a handheld sinus treatment device, wireless signals including control data from a personal electronic device. The method includes storing the control data in a memory of the handheld sinus treatment device. The method includes providing sinus relief treatment to the user in accordance with the control data with a current output circuit of the handheld sinus treatment device.

According to an embodiment, a method includes providing, with a personal electronic device, a graphical user interface configured to enable a user to select parameters for controlling a handheld sinus treatment device configured to provide sinus relief treatment stimulation to the user. The method includes receiving, via the graphical user interface, input data including parameters for operating the handheld sinus treatment device. The method includes transmitting wireless signals including control data from the personal electronic device to the handheld sinus treatment device in accordance with the input data. The control data includes instructions for operating the handheld sinus treatment device.

According to an embodiment, a system includes a personal electronic device configured to output wireless signals including control data for providing sinus relief treatment relief to the user. The system includes a handheld sinus treatment device. The handheld sinus treatment device includes a wireless receiver configured to receive the wireless signals from the personal electronic device and a current output circuit configured to provide sinus relief treatment stimulation to a treatment location on a face of the user.

BRIEF DESCRIPTION OF THE DRAWINGS

FIG. 9 is a flow diagram of a process for operating a handheld sinus treatment device, according to an embodiment.

DETAILED DESCRIPTION

Figure 1:
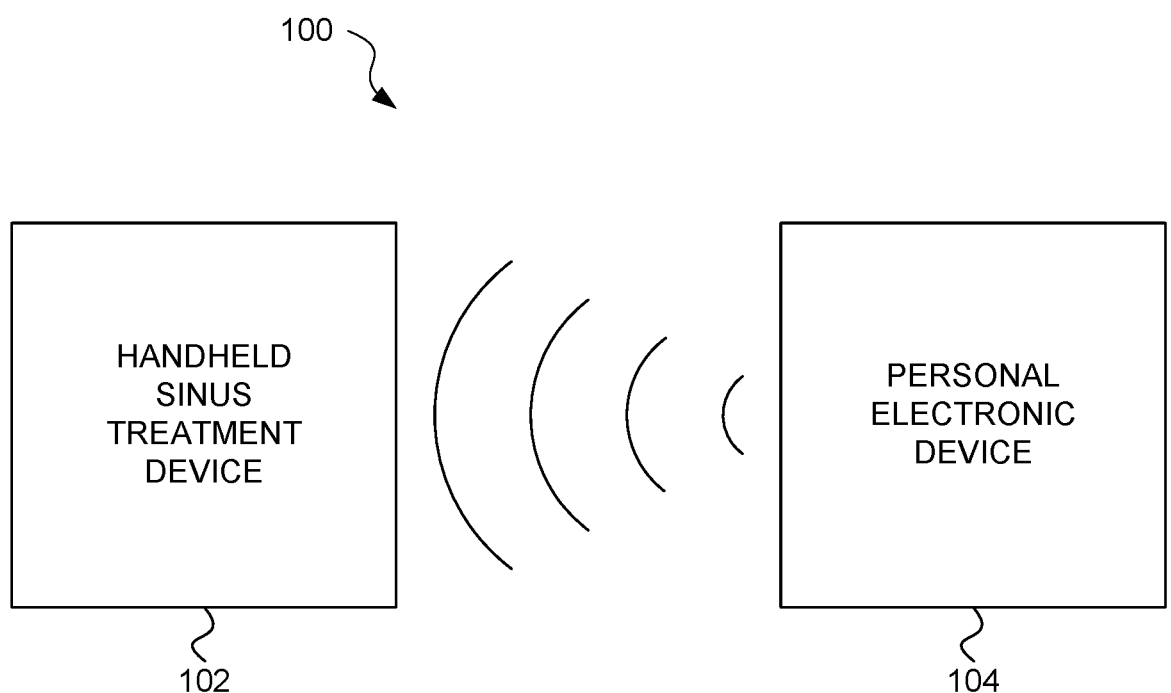
FIG. 1 is a block diagram of a sinus treatment system, according to an embodiment.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1 is a block diagram of a sinus treatment system 100, according to an embodiment. The sinus treatment system 100 includes a handheld sinus treatment device 102 and a personal electronic device 104. Together, the handheld sinus treatment device 102 and the personal electronic device 104 facilitate providing sinus relief treatment to a user. The handheld sinus treatment device 102 provides sinus relief treatment stimulation to treatment locations adjacent to the sinuses of the user. The handheld sinus treatment device 102 is configured to receive wireless signals including control data from the personal electronic device 104. The control data controls various operational parameters of the handheld sinus treatment device 102. The user of the sinus treatment system 100 can access a sinus treatment software application executed by the personal electronic device 104 in order to adjust various settings or parameters of the handheld sinus treatment device 102 and to control the activation of the handheld sinus treatment device 102. The personal electronic device 104 transmits wireless signals including control data to the handheld sinus treatment device 102 in accordance with the selections and commands of the user. The handheld sinus treatment device 102 receives the wireless signals and operates to provide sinus relief treatment to the user in accordance with the control data received from the personal electronic device 104.

According to an embodiment, the handheld sinus treatment device 102 is configured to provide sinus relief treatment to the user by providing electrical sinus treatment stimulation to treatment locations adjacent to the sinuses of the user. In a detection mode, the handheld sinus treatment device 102 detects a treatment location by outputting a detection signal to a treatment electrode of the handheld sinus treatment device 102 as the user glides the treatment electrode of the handheld sinus treatment device 102 over the skin adjacent to the sinuses of the user. The handheld sinus treatment device 102 identifies the treatment location based on the detection signal. When the handheld sinus treatment device 102 has identified a treatment location, the handheld sinus treatment device 102 enters into a treatment mode. In the treatment mode, the handheld sinus treatment device 102 provides sinus relief treatment stimulation to the treatment location, thereby providing sinus relief to the user. The user can operate the handheld sinus treatment device 102 to identify and provide treatment to multiple treatment locations.

According to an embodiment, the handheld sinus treatment device 102 includes a wireless receiver configured to receive the wireless signals from the personal electronic device 104. The wireless signals can control various parameters of the handheld sinus treatment device 102, including activation and deactivation of the handheld sinus treatment device 102, parameters of the detection mode of the handheld sinus treatment device 102, and parameters of the treatment mode of the handheld sinus treatment device 102.

According to an embodiment, the user of the handheld sinus treatment device 102 can access a software application executed by the personal electronic device 104 in order to adjust the settings of the handheld sinus treatment device 102 and to otherwise control the handheld sinus treatment device 102. The software application can enable the user to initiate a treatment session with the handheld sinus treatment device 102, to stop a treatment session with the handheld sinus treatment device 102, to adjust a sensitivity threshold of the handheld sinus treatment device 102 during the detection mode of the handheld sinus treatment device 102, and to adjust the parameters of the sinus treatment stimulation provided by the handheld sinus treatment device 102 during the treatment mode of the handheld sinus treatment device 102. The control data can control the manner in which the handheld sinus treatment device 102 provides sinus relief treatment to the user.

According to an embodiment, the handheld sinus treatment device 102 includes a microcontroller and a memory. When the handheld sinus treatment device 102 receives wireless signals including control data from the personal electronic device 104 via the wireless receiver, the microcontroller processes the wireless signals and writes the control data to the memory. The microcontroller then controls the operation of the handheld sinus treatment device 102 in accordance with instructions stored in the memory as received with the wireless signals.

Figure 2A:
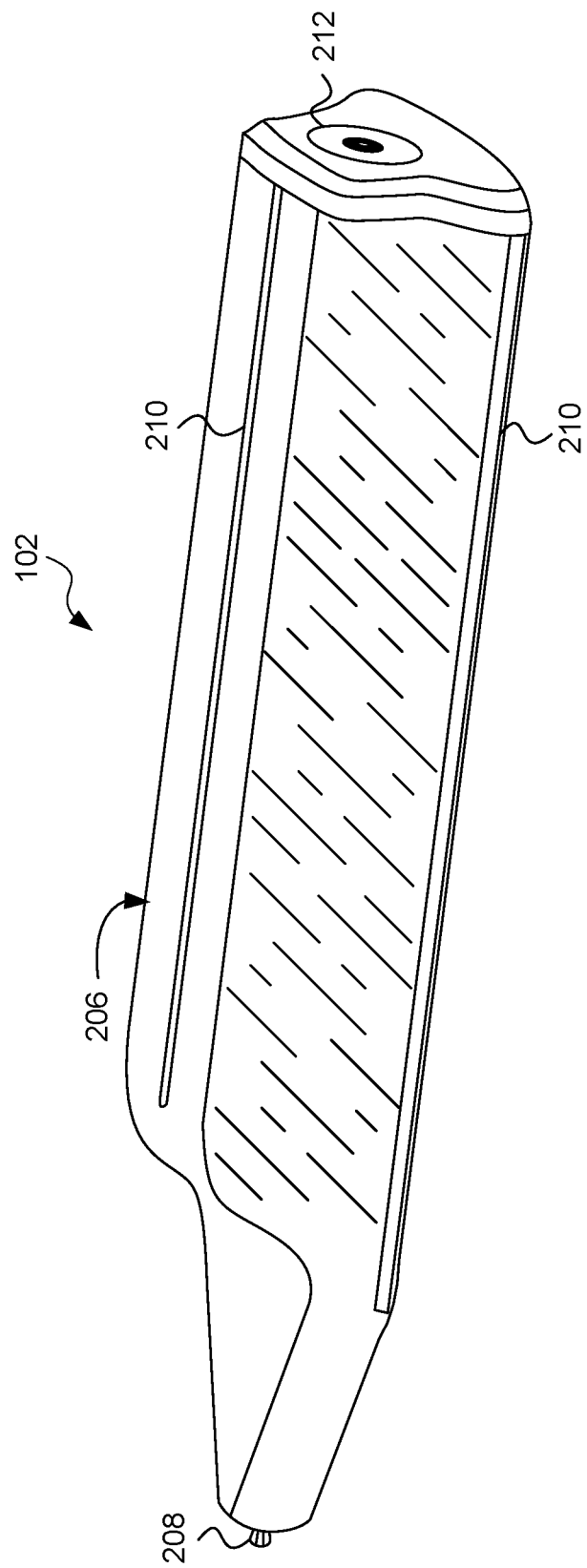
FIG. 2A is a perspective view of a handheld sinus treatment device, according to an embodiment.

FIG. 2A is a perspective view of a handheld sinus treatment device 102, according to an embodiment. The handheld sinus treatment device 102 includes a body 206, a treatment electrode 208, a return electrode 210, and a charging port 212, according to an embodiment.

According to an embodiment, the body 206 is a rigid casing. The body 206 has a shape that enables a user of the handheld sinus treatment device 102 to securely grip and comfortably hold the handheld sinus treatment device 102 during operation of the handheld sinus treatment device 102. The body 206 can be made from a material that is not electrically conductive. The body 206 can be made from a material that has low thermal conductivity. The body 206 is configured to protect sensitive electronic circuitry positioned within the body 206, as is described in more detail with relation to FIG. 3.

According to an embodiment, the treatment electrode 208 is an electrical conductor placed at a tip of the body 206. The treatment electrode 208 can include a rounded shape at a point of contact with the skin of the user such that the treatment electrode 208 can be placed against the skin of the user comfortably without piercing or scratching the skin. Furthermore, the shape and material of the treatment electrode 208 can be selected to enable the user to comfortably glide the treatment electrode 208 along the skin of the user's face adjacent to sinuses of the user.

According to an embodiment, the return electrode 210 includes an electrically conductive material positioned at various locations on or in the body 206. The return electrode 210 can be positioned in the body 206 at positions selected so that when the user holds the handheld sinus treatment device 102 in the user's hand, the user's hand is in contact with the return electrode 210 on one or more locations on the body 206. According to an embodiment, the return electrode 210 can include a conductive polycarbonate.

According to an embodiment, the charging port 212 is positioned at the rear of the body 206 of the handheld sinus treatment device 102. The charging port 212 is configured to receive a charging cable. When the charging cable is connected to the charging port 212, the internal battery of the handheld sinus treatment device 102 is recharged. Additionally, or alternatively, the charging port 212 can be a power supply port configured to connect to a power cable that provides power to the handheld sinus treatment device 102 while the user is using the handheld sinus treatment device 102. The charging port 212 can be a micro USB port, a USB 2.0 port, a USB 3.0 port, a USB C port, or any other kind of port that can be utilized to charge the battery of the handheld sinus treatment device 102, or to otherwise provide power to the handheld sinus treatment device 102. Additionally, or alternatively, the handheld sinus treatment device 102 can include wireless charging capability. For example, the handheld sinus treatment device 102 can include circuitry that enables inductive charging of the battery of the handheld sinus treatment device 102 such that when the handheld sinus treatment device 102 is positioned on a charging dock, the battery is recharged by inductive charging.

Figure 2B:
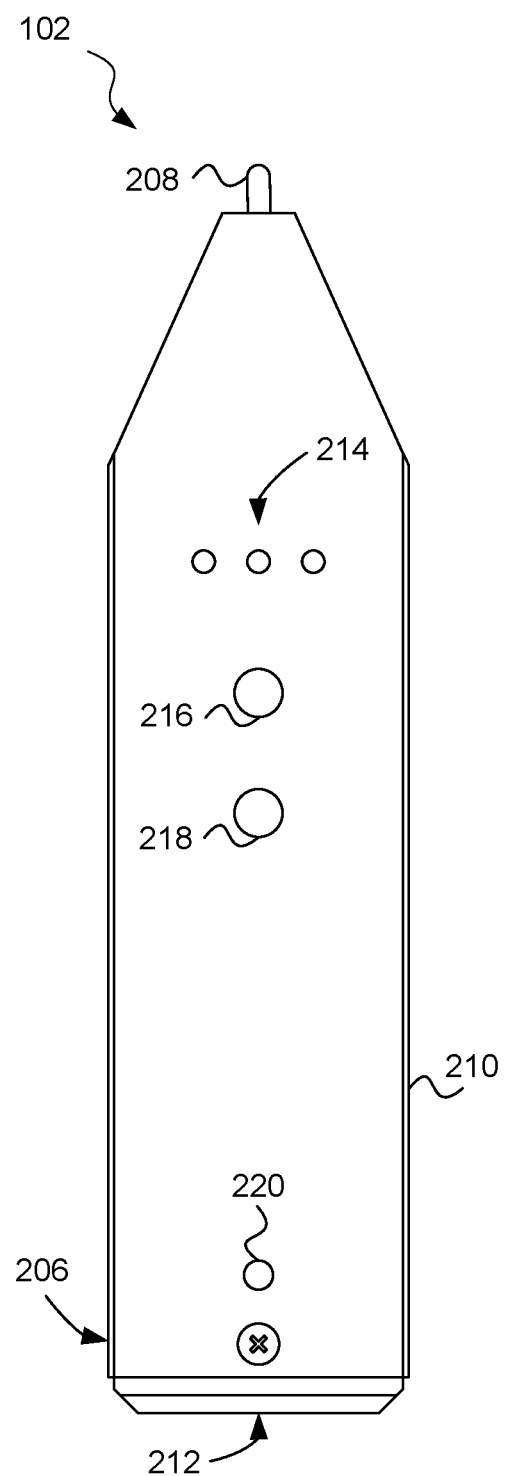
FIG. 2B is a top view of the handheld sinus treatment device of FIG. 2A, according to an embodiment.

FIG. 2B is a top view of a handheld sinus treatment device 102, according to an embodiment. The top view of the handheld sinus treatment device 102 illustrates the body 206, the treatment electrode 208, the return electrode 210, indicators 214, a sensitivity setting button 216, a power button 218, and a low battery indicator 220.

According to an embodiment, the indicators 214 can provide an indication of the sensitivity level of the handheld sinus treatment device 102. The sensitivity level corresponds to a sensitivity setting for detecting treatment areas adjacent to the sinuses of the user. The indicators 214 can include multiple LED indicators. The handheld sinus treatment device 102 can illuminate a number of the sensitivity level indicator LEDs to indicate a sensitivity level of the handheld sinus treatment device 102 during a detecting mode. A greater number of illuminated indicator LEDs can correspond to a higher sensitivity level. A lesser number of illuminated indicator LEDs can correspond to a lower sensitivity level. Alternatively, other schemes for illuminating LEDs to indicate a sensitivity level of the detecting mode of the handheld sinus treatment device 102 can be utilized. Additionally, the indicators 214 can include indicators other than LEDs. For example, the indicators 214 can include various types of lights, a display panel, or other types of indicators capable of providing an indication of the sensitivity level of the handheld sinus treatment device 102 during a detecting mode of the handheld sinus treatment device 102. According to an embodiment, the indicators 214 can also signal that a treatment location has been identified, that treatment stimulation is currently being provided, that another treatment location should be identified, or other parameters of operation of the handheld sinus treatment device 102.

According to an embodiment, the sensitivity setting button 216 is configured to enable the user to adjust the sensitivity of the handheld sinus treatment device 102 during a detecting mode. The user can manipulate the sensitivity setting button 216 in order to increase or decrease the sensitivity of the handheld sinus treatment device 102. For example, the user can press the sensitivity setting button 216 to adjust the sensitivity of the handheld sinus treatment device 102. Additionally, or alternatively, the user can toggle or slide the sensitivity setting button 216 in order to adjust the sensitivity of the handheld sinus treatment device 102. Additionally, or alternatively, the sensitivity setting button 216 can include multiple buttons for adjusting the sensitivity of the handheld sinus treatment device 102. A first button can be used to decrease the sensitivity. A second button can be used to increase the sensitivity. Additionally, or alternatively, the handheld sinus treatment device 102 can include a touchscreen that enables the user to adjust the sensitivity of the handheld sinus treatment device 102.

According to an embodiment, the power button 218 is configured to enable the user to turn the handheld sinus treatment device 102 on or off. For example, if the handheld sinus treatment device 102 is currently off, then the user can turn the handheld sinus treatment device 102 on by pressing, toggling, sliding, or otherwise manipulating, the power button 218. If the handheld sinus treatment device 102 is currently on, then the user can turn the handheld sinus treatment device 102 off by pressing, toggling, sliding, or otherwise manipulating the power button 218. Alternatively, the sensitivity setting button 216 and the power button 218 can be implemented in a single button or switch that can adjust the sensitivity or turn the handheld sinus treatment device 102 on or off based on a length of a button press, a number of button presses, or other types of manipulations of the single button.

According to an embodiment, the low battery indicator 220 can provide an indication of a state of charge of the battery of the handheld sinus treatment device 102. The low battery indicator 220 can include one or more LEDs. When the battery of the handheld sinus treatment device 102 is low, one or more LEDs of the low battery indicator 220 can become illuminated. If the low battery indicator 220 includes a single LED, then the single LED can become illuminated when the battery is nearing depletion. Conversely, the single LED may not be illuminated when the battery is not nearing depletion. Alternatively, when the battery is nearing depletion, a first LED of a first color can be illuminated to indicate that the battery is nearing depletion. If the battery is not nearing depletion, then a second LED of a second color can be illuminated indicating that the battery is not nearing depletion.

According to an embodiment, portions of the return electrode 210 are positioned on the sides of the body 206 of the handheld sinus treatment device 102. When the user grips the handheld sinus treatment device 102 such that a thumb of the user is in a position to manipulate the sensitivity setting button 216 and the power button 218, the palm and/or fingers of the hand of the user will be in contact with the portion of the return electrode 210 positioned on the sides of the body 206 of the handheld sinus treatment device 102.

Figure 2C:
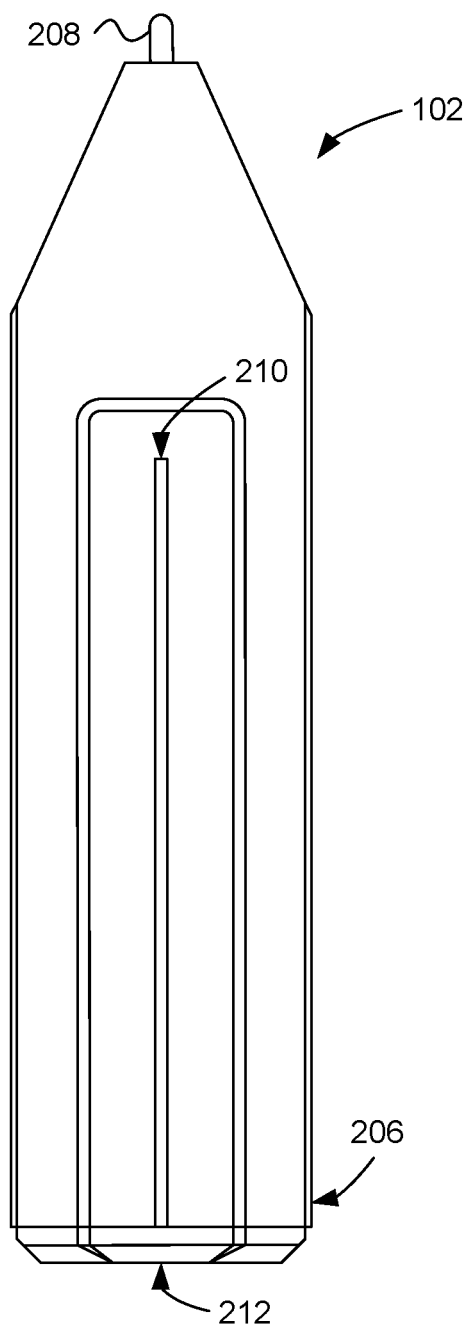
FIG. 2C is a bottom view of the handheld sinus treatment device of FIG. 2A, according to an embodiment.

FIG. 2C is a bottom view of the handheld sinus treatment device 102 of FIG. 2B, according to an embodiment. The bottom view of the handheld sinus treatment device 102 illustrates a portion of the return electrode 210 positioned on the bottom portion of the body 206 of the handheld sinus treatment device 102. The positioning of a portion of the return electrode 210 on the bottom of the body 206 of the handheld sinus treatment device 102 further ensures that when the user holds the handheld sinus treatment device 102 in the user's hand, the user's hand will be in contact with the return electrode 210.

Figure 2D:
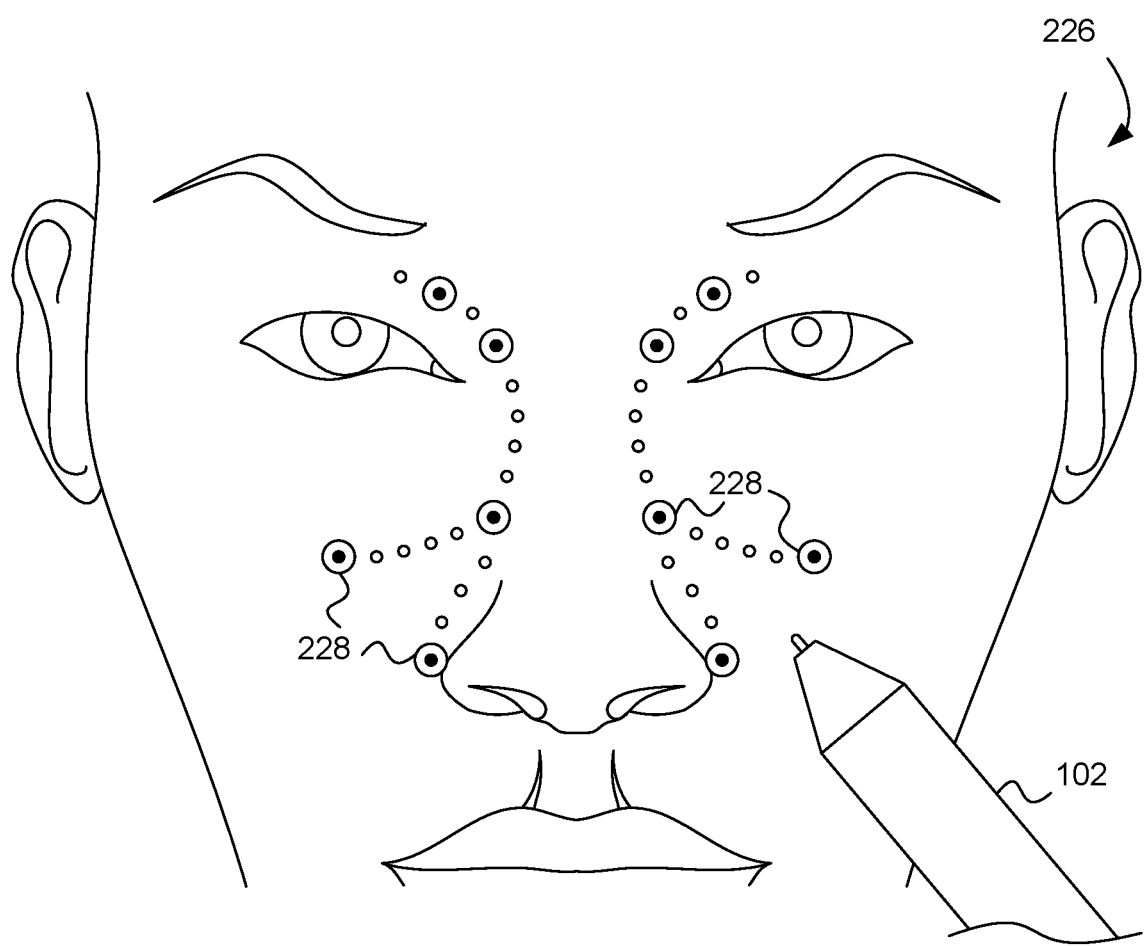
FIG. 2D is an illustration of a handheld sinus treatment device providing sinus relief treatment to highlighted treatment areas adjacent to the sinuses of a user, according to an embodiment.

FIG. 2D is an illustration of a face 226 of a user of the handheld sinus treatment device 102 highlighting treatment areas 228. According to an embodiment, the treatment areas 228 correspond to nerve nodes. The nerve nodes are locations 228 at which sinus nerves pass through the skull.

According to an embodiment, a user uses the handheld sinus treatment device 102 by holding the body 206 in one hand such that the user's hand is in contact with portions of the return electrode 210. The user then places the treatment electrode 208 on the skin adjacent to the sinuses and glides the treatment electrode 208 over the skin during a detection mode of the handheld sinus treatment device 102. In the detection mode, the handheld sinus treatment device 102 detects the location 228 of a nerve node beneath the skin. When the handheld sinus treatment device 102 detects the location 228 of a nerve node beneath the skin, the handheld sinus treatment device 102 can enter a treatment mode.

According to an embodiment, in the treatment mode, the handheld sinus treatment device 102 provides treatment stimulation to the treatment location 228, corresponding to the nerve that is located during the detection mode. The handheld sinus treatment device 102 can provide treatment stimulation to the treatment location 228 by providing electrical stimulation to the treatment location 228. The electrical stimulation can affect the nerve node in such a way that the user experiences relief from troubling sinus symptoms such as pain, congestion, inflammation, or other unpleasant symptoms.

According to an embodiment, the handheld sinus treatment device 102 is a transcutaneous electrical nerve stimulation (TENS) device. The handheld sinus treatment device 102 applies electrical treatment stimulation in the form of a microcurrent having selected characteristics. The microcurrent can have an average magnitude that is multiple orders of magnitude lower than common TENS devices. According to an embodiment, the microcurrent does not have a DC component, but is characterized by current spikes of alternating polarity. According to an embodiment, the treatment stimulation is provided at each treatment location 228 for a period of time between 2-10 seconds.

According to an embodiment, the treatment electrode 208 is the active electrode of a monopolar design. The housing/body 206 of the handheld sinus treatment device 102 may serve as the return electrode when return electrodes 210 are integrated into the body 206. A user's hand holding the handheld sinus treatment device 102 completes the electrical path from the conductive treatment electrode 208 to the return electrode(s) 210 in that microcurrents may travel from conductive treatment electrode 208, through the nasal area of a user and down to the hand of the user that is contacting the return electrode(s) 210, in an embodiment. These microcurrents may be referred to as "stimulation currents" in this disclosure.

According to an embodiment, in the detection mode, the user presses the conductive treatment electrode 208 to the skin and the handheld sinus treatment device 102 initiates a low-frequency circuit that is maintained at a constant current. The handheld sinus treatment device 102 may use the current to calculate the impedance in the path between the tissue at the treatment electrode 208 and the hand in contact with the device 102. The handheld sinus treatment device 102 remains in the detection mode until the detection current indicates that the impedance is below a threshold impedance. The position of the treatment electrode 208 when the impedance is below the threshold impedance corresponds to a treatment area 228. The treatment area 228 corresponds to a nerve node area. When the handheld sinus treatment device 102 identifies a treatment area 228 based on the calculated impedance, the handheld sinus treatment device 102 can enter the treatment mode and can deliver treatment stimulation to the identified treatment area 228.

According to an embodiment, the handheld sinus treatment device 102 can indicate to the user that the handheld sinus treatment device 102 the treatment mode and that the user should hold the treatment electrode 208 at the treatment location 228 for a selected period of time. According to an embodiment, the handheld sinus treatment device 102 can indicate the transition between the detection mode and the treatment mode by the indicators 214. The indicators 214 can include one or more LEDs that can provide an illumination scheme that indicates whether the handheld sinus treatment device 102 is in the detection mode or the treatment mode. According to an embodiment, the handheld sinus treatment device 102 can indicate that the handheld sinus treatment device 102 is in the treatment mode via haptic feedback (vibration). According to an embodiment, the handheld sinus treatment device 102 can indicate whether the handheld sinus treatment device 102 is in the detection mode, the treatment mode, or transitioning between the detection and treatment nodes by a combination of haptic feedback and LED indicators 214. According to an embodiment, when the handheld sinus treatment device 102 enters the treatment mode as indicated by one or more of LED indicators 214 and haptic feedback, the user holds the device 102 in place until the treatment period has passed as indicated by cessation of haptic and LED indicators 214 (approximately 8 seconds in one example).

According to an embodiment, once the treatment period ends, the handheld sinus treatment device 102 resets to detection mode. The user then may continue to glide the handheld sinus treatment device 102 along the indicated path until reaching the next treatment area 228 as identified based on impedance calculations. The user may adjust the impedance sensitivity of the handheld sinus treatment device 102, in one embodiment. Changes in sensitivity adjust the impedance threshold at which the handheld sinus treatment device 102 will enter treatment mode. Changes in sensitivity do not change the output current, in one embodiment.

According to an embodiment, the spring-loaded tip activates the circuit and gently ramps the current to provide maximal comfort to user.

According to an embodiment, constant current stimulation circuit output is directed to the active electrode 208 (the device tip) and returned to the circuit by way of the return electrode 210 (metallized portions of the enclosure). When the circuit is completed by the user pressing the device tip 208 to the face, a microcontroller monitors the resulting stimulation current and controls the stimulation voltage (across the treatment electrode 208 and return electrode 210) to maintain the desired current, in one embodiment. The impedance of the circuit is then calculated and monitored by the microcontroller. In the event that the impedance falls below a specified threshold, which is indicative of a treatment point, the microcontroller presents a treatment prompt through the user interface (UI), in one embodiment. According to an embodiment, the user is instructed to maintain the tip location until the treatment prompt has timed out. After treatment time out, the user is instructed to slowly move the tip 208 to the next detected treatment point, in one embodiment.

According to an embodiment, the sensitivity level setting determines the impedance threshold at which the device 102 will signal the user to detection of a treatment point. The treatment sensitivity threshold may be increased to compensate for higher impedance associated with dry skin or the presence of makeup, in one embodiment. Upon detection of a treatment point, the haptic motor starts to vibrate and the sensitivity level LEDs 214 flash for a pre-programmed period of time, in one embodiment. If the calculated impedance increases above the threshold (tip 208 removed from the face or moved to a higher impedance location on the face), the treatment session may be terminated.

According to an embodiment, the handheld sinus treatment device 102 operates under the control of the personal electronic device 104. The handheld sinus treatment device 104 includes a wireless receiver by which the handheld sinus treatment device 102 receives wireless signals from the personal electronic device 104. The personal electronic device 104 can include a software application that enables the user to adjust the settings and control the operation of the handheld sinus treatment device 102. The user can operate the personal electronic device 104 to adjust the threshold impedance by which treatment areas 228 are identified, to adjust the duration of treatment stimulation, to adjust the strength of the treatment stimulation, to adjust how frequently treatments should be applied, to enter training modes by which treatment locations 228 are identified and recorded, to power on and off the handheld sinus treatment device 102, to set the types of indicators that the handheld sinus treatment device 102 will utilize in signaling to the user the various modes of operation of the handheld sinus treatment device 102.

Figure 3:
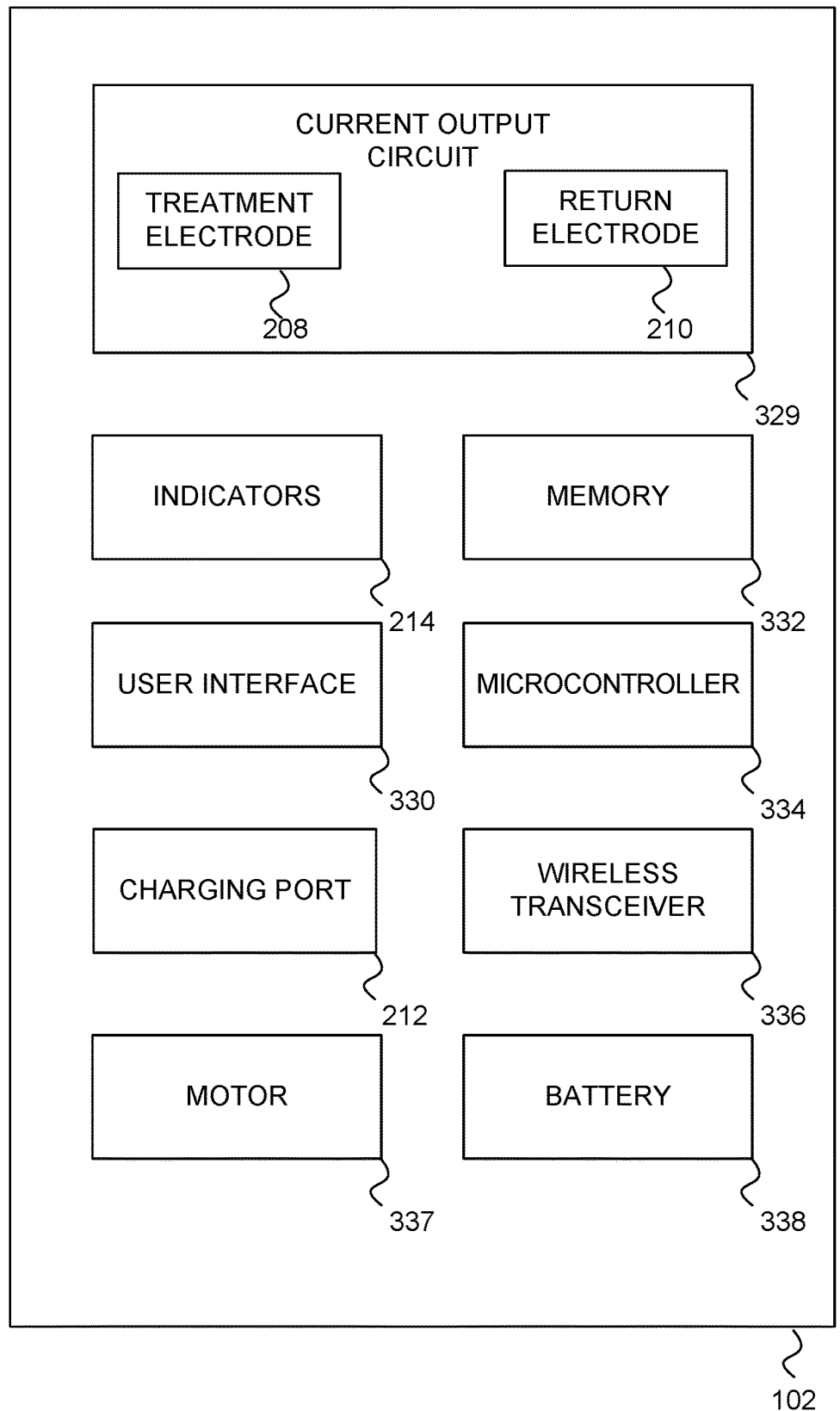
FIG. 3 is a block diagram of a handheld sinus treatment device, according to an embodiment.

FIG. 3 is a block diagram of the handheld sinus treatment device 102, according to an embodiment. The handheld sinus treatment device 102 includes a current output circuit 329, the charging port 212, indicators 214, a user interface 330, a memory 332, a microcontroller 334, a wireless transceiver 336, a motor 337 (not shown), and a battery 338. The current output circuit 329 includes the treatment electrode 208 and the return electrode 210. The handheld sinus treatment device 102 utilizes these components to provide effective sinus relief treatments to the user.

According to an embodiment, the treatment electrode 208 and the return electrode 210 cooperate together to provide both detection currents and treatment stimulation. Detection and treatment currents are passed between the treatment electrode 208 and the return electrode 210 through the body of the user. In particular, the treatment electrode 208 is positioned in contact with the user's skin to the sinus areas of the user. The return electrode 210 is in contact with the user's hand as the user holds the handheld sinus treatment device 102. The detection and treatment currents pass between the treatment electrode 208 and return electrode 210 via the hand, body, and facial skin of the user.

According to an embodiment, the indicators 214 provide indications to the user as to the current mode of operation of the handheld sinus treatment device 102. Indicators 214 can include one or more LEDs that can be illuminated in selected ways to indicate whether the handheld sinus treatment device 102 is powered on, whether the handheld sinus treatment device 102 is in a treatment mode, whether the handheld sinus treatment device 102 is in a detection mode, whether the handheld sinus treatment device 102 awaits user input, whether the handheld sinus treatment device 102 is communicating with the personal electronic device 104, or indications of other types of functionality of the handheld sinus treatment device 102. According to an embodiment, the indicators 214 can include a display capable of outputting text or images to indicate to the user the various functions of the handheld sinus treatment device 102.

According to an embodiment, the user interface 330 includes various components that enable the user to control functionality of the handheld sinus treatment device 102. The user interface 330 can include the on-off button 218, the sensitivity setting button 216, or other kinds of buttons, switches, touchscreens, or input controls that enable the user to control functionality of the handheld sinus treatment device 102. The user can manipulate the user interface 330 in order to control the functionality of the handheld sinus treatment device 102.

According to an embodiment, the memory 332 stores data related to the functionality of the handheld sinus treatment device 102. The memory 332 can include software instructions by which the various functionalities of the handheld sinus treatment device 102 can be implemented. The memory 332 can include reference impedance values and/or threshold impedance values. The reference and threshold impedance values can be utilized in the detection mode of the handheld sinus treatment device 102. The memory 332 can include data indicating previously detected treatment locations 228. The memory 332 can include other settings such as treatment lengths, treatment stimulation strengths, frequencies of treatments, or other settings including default settings and user selected settings for operation of the handheld sinus treatment device 102. The memory 332 can include one or more of EEPROMs, flash memory, ROMs, SRAM, DRAM, or other kinds of computer readable media capable of storing instructions that can be executed by the microcontroller 334.

According to an embodiment, the wireless transceiver 336 is configured to receive wireless signals from the personal electronic device 104. The wireless transceiver 336 can receive wireless signals from the personal electronic device 104 to control the functionality of the handheld sinus treatment device 102. The wireless signals can include signals that adjust the settings and control the operation of the handheld sinus treatment device 102. The wireless signals can include data or instructions that cause the handheld sinus treatment device 102 to adjust the threshold impedance by which treatment areas 228 are identified. The wireless signals can include data or instructions that cause the handheld sinus treatment device 102 to adjust the duration of treatment stimulation. The wireless signals can include data or instructions that cause the handheld sinus treatment device 102 to adjust the strength of the treatment stimulation. The wireless signals can include data or instructions that cause the handheld sinus treatment device 102 to adjust how frequently treatments should be applied. The wireless signals can include data or instructions that cause the handheld sinus treatment device 102 to enter training modes by which treatment locations 228 are identified and recorded. The wireless signals can include data or instructions that cause the handheld sinus treatment device 102 to power on and off the handheld sinus treatment device 102. The wireless signals can include data or instructions that cause the handheld sinus treatment device 102 to set the types of indicators that the handheld sinus treatment device 102 will utilize in signaling to the user the various modes of operation of the handheld sinus treatment device 102.

According to an embodiment, the wireless transceiver 336 transmits wireless signals to the personal electronic device 104 indicating the status of the handheld sinus treatment device 102. The wireless receiver 336 can transmit wireless signals that indicate whether previously received wireless commands have been executed. The wireless transceiver 336 can transmit wireless signals that indicate whether the handheld sinus treatment device 102 is functioning properly. The wireless transceiver 336 can transmit wireless signals that indicate whether the handheld sinus treatment device 102 is in an error state. The wireless transceiver 336 can transmit wireless signals that provide other kinds of indications to the personal electronic device 104.

According to an embodiment, the wireless transceiver 336 is an RF transceiver. According to an embodiment, the wireless receiver 336 implements a Bluetooth protocol. According to an embodiment, the wireless transceiver 336 implements a Zigbee protocol. According to an embodiment, the wireless transceiver 336 implements a Wi-Fi protocol. The wireless transceiver 336 can operate in accordance with other protocols. The wireless transceiver 336 can be a wireless transceiver other than an RF transceiver. According to an embodiment, the wireless transceiver 336 is instead a wireless receiver capable only of receiving wireless signals from the personal electronic device 104.

According to an embodiment, the motor 337 enables the handheld sinus treatment device 102 to provide haptic feedback to the user. For example, during a treatment mode in which the handheld sinus treatment device 102 provides stimulation treatment to a treatment area 228, the motor 337 can cause the handheld sinus treatment device 102 to vibrate mildly to indicate to the user that the handheld sinus treatment device 102 is in the treatment mode. The motor 337 can cease the vibration to indicate that the handheld sinus treatment device 102 is no longer in the treatment mode. The motor 337 can generate vibrations to provide a variety of types of indications to the user of the handheld sinus treatment device 102.

According to an embodiment, the battery 338 provides power to the handheld sinus treatment device 102. The battery 338 can include a rechargeable battery that enables the user to recharge the battery 338 after the battery 338 has become depleted through use. The battery 338 can be a lithium-ion battery, a NiCad battery, a carbon zinc battery, an alkaline battery, a nickel metal hydride battery, or other types of batteries.

According to an embodiment, the charging port 212 enables the user to recharge the battery 338. For example, the charging port 212 can be configured to receive a charging cable that connects the charging port 212 to a power source. Charging port 212 can include a micro USB port, a USB 2.0 port, a USB 3.0 port, a USB C port, or other types of charging ports. According to an embodiment, the charging port 212 enables charging and data transmission.

When a charging cable is plugged into the charging port 212, the battery 338 can be charged and data can be received or transmitted over the charging cable via the charging port 212. According to an embodiment, the handheld sinus treatment device 102 can operate while a charging cable is attached to the charging port 212. Thus, if the battery 338 is depleted, the user can attach a charging cable to the charging port 212 and can operate the handheld sinus treatment device 102 from power received via the charging port 212.

According to an embodiment, the microcontroller 334 controls the functionality of the other components of the handheld sinus treatment device 102. The microcontroller 334 is communicatively coupled to the treatment electrode 208, the return electrode 210, the indicators 214, the memory 332, the user interface 330, the wireless transceiver 336, and the charging port 212.

According to an embodiment, the microcontroller 334 executes the software instructions stored in the memory 332 to implement the various modes of functionalities of the handheld sinus treatment device 102. The microcontroller causes the treatment electrode 208 and the counter electrode 210 to pass the detection currents in the detection mode, and to pass the treatment stimulation currents in the treatment mode. The microcontroller 334 controls the indicators 214 to indicate the various modes of functionalities of the handheld sinus treatment device 102. The microcontroller 334 communicates with the user interface 330 to enable the user to select various modes of operation of the handheld sinus treatment device 102. The microcontroller 334 controls the functionality of the wireless transceiver 336.

According to an embodiment, when wireless signals are received by the wireless transceiver 336 from the personal electronic device 104, the microcontroller 334 receives and processes the wireless signals. The microcontroller 334 can execute instructions contained in the wireless signals. The microcontroller 334 can write to the memory 332 control data received in the wireless signals. The microcontroller 334 can read data from the memory 332 in accordance with instructions received in the wireless signals.

Figure 4:
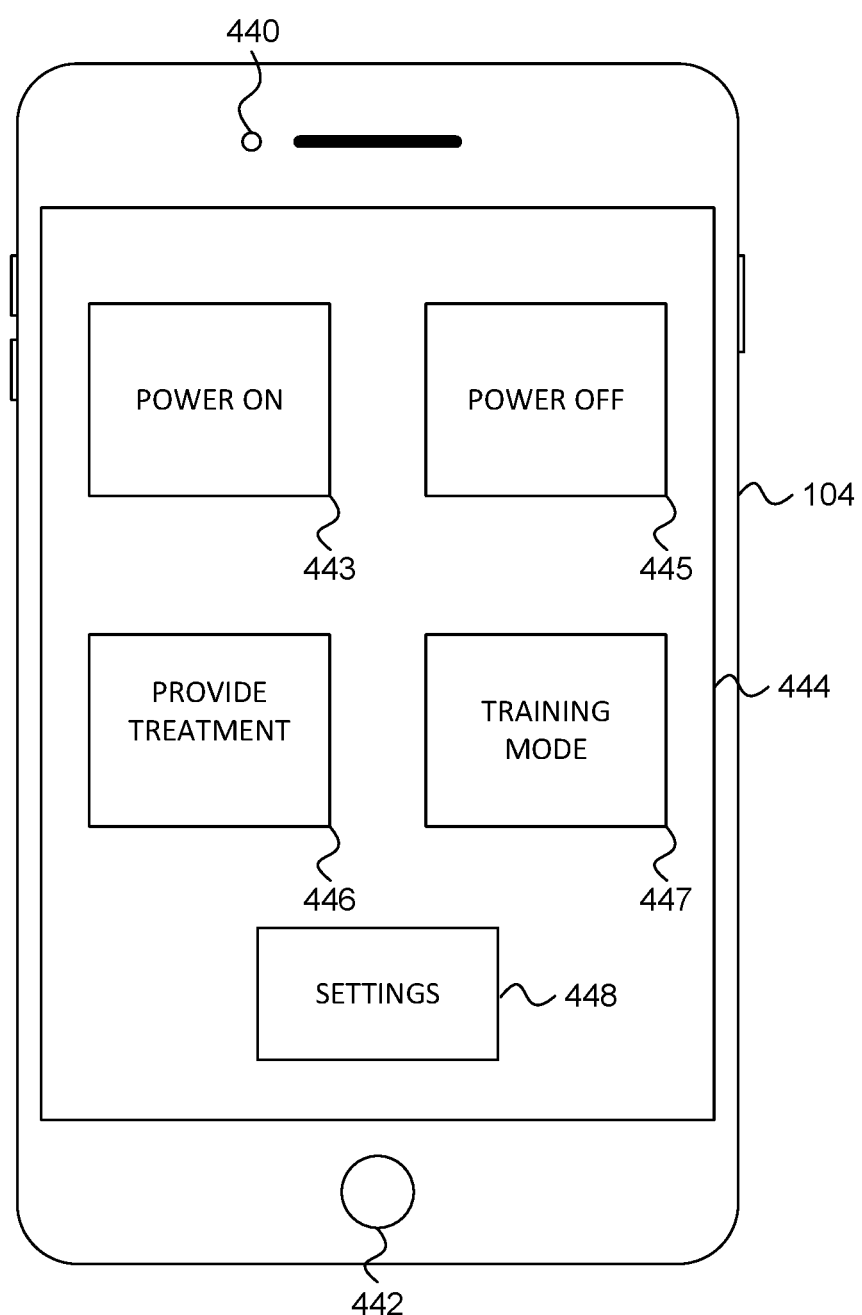
FIG. 4 is an illustration of a personal electronic device executing an aspect of a software application for controlling a handheld sinus treatment device, according to an embodiment.

FIG. 4. is an illustration of a personal electronic device 104, according to an embodiment. The personal electronic device 104 is a computing device configured to be used by the user to control and communicate with the handheld sinus treatment device 102. The personal electronic device 104 transmits wireless signals to the handheld sinus treatment device 102 in order to communicate with and control the handheld sinus treatment device 102.

In the illustration of FIG. 4, the personal electronic device 104 is a mobile phone. Alternatively, the personal electronic device 104 is a a tablet, a laptop computer, a desktop computer, an MP3 player, a wearable device, such as a smart watch, or another kind of personal electronic device capable of transmitting wireless signals to the handheld sinus treatment device 102. The personal electronic device 104 includes a camera 440, a button 442, and a touchscreen display 444.

According to an embodiment, the personal electronic device 104 includes a software application configured to enable the personal electronic device 104 to communicate with the handheld sinus treatment device 102. The personal electronic device 104 executes the software application. When the personal electronic device 104 executes the software application, upon being selected by the user, the personal electronic device 104 presents a graphical user interface on the touchscreen display 444. The graphical user interface enables the user to select icons, menus, drop-down menus, text boxes, or other graphical user interface functionality that enables the user to make selections as to how the user would like to control the handheld sinus treatment device 102.

According to an embodiment, the graphical user interface includes a power on icon 443, a power off icon 445, a provide treatment icon 446, a training mode icon 447, and a settings icon 448. The power on icon 443 enables the user to turn on the handheld sinus treatment device 102. The power off icon 445 enables the user to turn off the handheld sinus treatment device 102. The provide treatment icon 446 enables the user to activate a treatment session of the handheld sinus treatment device 102. The training mode icon 447 enables the user to activate a training mode of the handheld sinus treatment device 102.

The settings icon 448 enables the user to access various settings of the handheld sinus treatment device 102 and to adjust them. Those of skill in the art will recognize, in light of the present disclosure, that many other configurations of a graphical user interface can be implemented in accordance with principles of the present disclosure. All such other configurations fall within the scope of the present disclosure According to an embodiment, the software application enables the user to adjust the threshold impedance by which treatment areas 228 are identified in the detection mode of the handheld sinus treatment device 102. The graphical user interface can present the user with options to raise the threshold impedance. With increased threshold impedance, the handheld sinus treatment device 102 can identify treatment areas 228 that might not be identified as treatment areas 228, because areas 228 with higher impedance will now fall below the threshold impedance. The graphical user interface can present the user with options to reduce the threshold impedance. With decreased threshold impedance, the handheld sinus treatment device 102 will be more selective in identifying treatment areas 228 because only areas within impedance that are lower than the reduced threshold impedance will be identified as treatment areas 228. When the user selects a new threshold impedance, the personal electronic device 104 transmits wireless signals including data indicating the new selected threshold impedance. The handheld sinus treatment device 102 receives the wireless signals including the data indicating the new selected threshold impedance. The microcontroller 334 writes the new threshold impedance to the memory 332. The handheld sinus treatment device 102 operates the detection mode in accordance with the new threshold impedance.

According to an embodiment, the graphical user interface may present to the user an option to increase or decrease the sensitivity of the detection mode instead of specifically enabling the user to increase or decrease the threshold impedance. Increasing or decreasing the sensitivity of the detection mode can have the same effect as increasing or decreasing the threshold impedance, but the user may not be presented with the term threshold impedance as the term may be confusing to some users.

According to an embodiment, the software application enables the user to adjust the duration of treatment stimulation. As discussed previously, when the handheld sinus treatment device 102 identifies a treatment area 228 during the detection mode, the handheld sinus treatment device 102 enters a treatment mode by which treatment stimulation is provided to the treatment area 228. The handheld sinus treatment device 102 may initially have a default treatment stimulation length. The default treatment stimulation length may be between five and 10 seconds. The software application executed by the personal electronic device 104 enables the user to adjust the duration of the treatment stimulation. The software application can enable the user to increase the length of the treatment stimulation. The software application can enable the user to decrease the length of the treatment stimulation. When the user has made selections adjusting the length of the treatment stimulation, the personal electronic device 104 transmits wireless signals to the handheld sinus treatment device 102 including data indicating the newly selected length of the treatment stimulation. The microcontroller 334 processes the wireless signal and writes the newly selected length of treatment stimulation to the memory 332. When the user next uses the handheld sinus treatment device 102, the handheld sinus treatment device 102 will provide treatment simulations in accordance with the selected treatment stimulation length.

According to an embodiment, the software application enables the user to adjust the strength of the treatment stimulation. As discussed previously, when the handheld sinus treatment device 102 provides treatment stimulation to a treatment area 228, the handheld sinus treatment device 102 passes a treatment current through the nerve node corresponding to the treatment location 228. The software application enables the user to adjust the magnitude of the treatment current, or to otherwise adjust the strength of the treatment stimulation provided by the handheld sinus treatment device 102. When the user has made selections adjusting the strength of the treatment stimulation, the personal electronic device 104 transmits wireless signals to the handheld sinus treatment device 102 including data indicating the newly selected strength of the treatment stimulation. The microcontroller 334 processes the wireless signal and writes the newly selected strength of the treatment stimulation to the memory 332. When the user next uses the handheld sinus treatment device 102, the handheld sinus treatment device 102 will provide treatment stimulation in accordance with the selected treatment stimulation strength.

According to an embodiment, the software application enables the user to adjust how frequently treatments should be applied. The handheld sinus treatment device 102 may come with a default recommendation for frequency with which sinus relief treatments should be applied. For example, the handheld sinus treatment device 102 may come with the recommendation that the user provide sinus relief treatments twice daily. The software application may prompt or otherwise remind the user to utilize the handheld sinus treatment device 102 in accordance with the default recommended frequency. However, the software application enables the user to adjust the frequency with which sinus relief treatments should be applied by the user. After the user has adjusted the frequency, the personal electronic device 104 may provide prompts or other kinds of reminders to the user to utilize the handheld sinus treatment device 102 in accordance with the adjusted frequency selected by the user.

According to an embodiment, the software application enables the user to enter a training mode 447 by which treatment locations 228 are identified and recorded. When the user selects the training mode 447 via the graphical user interface provided by the personal electronic device 104, the personal electronic device 104 transmits wireless signals to the handheld sinus treatment device 102 initiating the training mode 447. In the training mode 447, the personal electronic device 104 instructs the user to operate the handheld sinus treatment device 102. The personal electronic device 104 may instruct the user to position the treatment electrode 208 at a particular location 228 on the user's face 226 and to glide the treatment electrode 208 on the skin until the handheld sinus treatment device 102 indicates that a treatment location 228 has been identified. The personal electronic device 104 may then instruct the user to continue gliding the treatment electrode 208 on the skin until the handheld sinus treatment device 102 has identified the next treatment location 228. In the training mode 447, the personal electronic device 104 can continue this process until a selected number of treatment locations 228 have been identified, or until the user wishes to exit the training mode 447. In the training mode 447, the personal electronic device 104 transmits wireless signals to the handheld sinus treatment device 102 directing the handheld sinus treatment device 102 to operate in the training mode 447. According to an embodiment, the training mode 447 can be utilized only to assist the user in identifying treatment locations 228 the user has been practicing using the handheld sinus treatment device 102 and the detection mode. Alternatively, the handheld sinus treatment device 102 can provide treatment stimulation to the treatment locations 228 during the training mode 447.

According to an embodiment, during the training mode 447, the personal electronic device 104 directs the user to hold the personal electronic device 104 so that the camera 440 may record a stream of images of the user's face 226 and the handheld sinus treatment device 102 during the training mode 447. The personal electronic device 104 can identify the positions on the user's face 226 that correspond to the treatment locations 228 identified during the training mode 447. When the user operates the handheld sinus treatment device 102 in the treatment mode 446, the user can view the touchscreen display 444 on the personal electronic device 104 to view the treatment locations 228 on the face of the user. This can assist the user to quickly direct the treatment electrode 208 to the positions on the user's face 226 corresponding to the previously identified treatment locations 228.

According to an embodiment, the software application enables the user to select an icon corresponding to a treatment mode 446. When the user selects the treatment mode 446, the personal electronic device 104 transmits wireless signals to the handheld sinus treatment device 102 causing the handheld sinus treatment device 102 to be ready to provide treatment stimulation. When the user selects the treatment mode 446, the handheld sinus treatment device 102 may first go into the detection mode until the user has placed the treatment electrode 208 against the treatment location 228. The handheld sinus treatment device 102 may then enter the treatment mode 446 in which the handheld sinus treatment device 102 applies treatment stimulation to the treatment location 228.

In one embodiment, the user can provide via the GUI, input data including data related to the user. The input data can include data regarding symptoms, such as sinus pain or sinus congestion, experienced by the user. In one embodiment, he data regarding medical symptoms of the user includes data regarding severity of symptoms. In one embodiment, the data regarding symptoms of the user includes data regarding frequency of symptoms. In one embodiment, the application generates the instructions for operating the handheld sinus treatment device based in part on the medical symptoms of the user.

In one embodiment, entering, via the personal electronic device, the severity of their symptoms before and after treatment, users can follow their progress. The personal electronic device 104 can cause the handheld sinus treatment device can also to adapt to a positive or negative clinical outcome from treatment as reported by the user by changing the stimulation parameters for subsequent treatments. The changes can include one or more the impedance threshold, current amplitude, the frequency, and the waveform shape.

Figure 5:
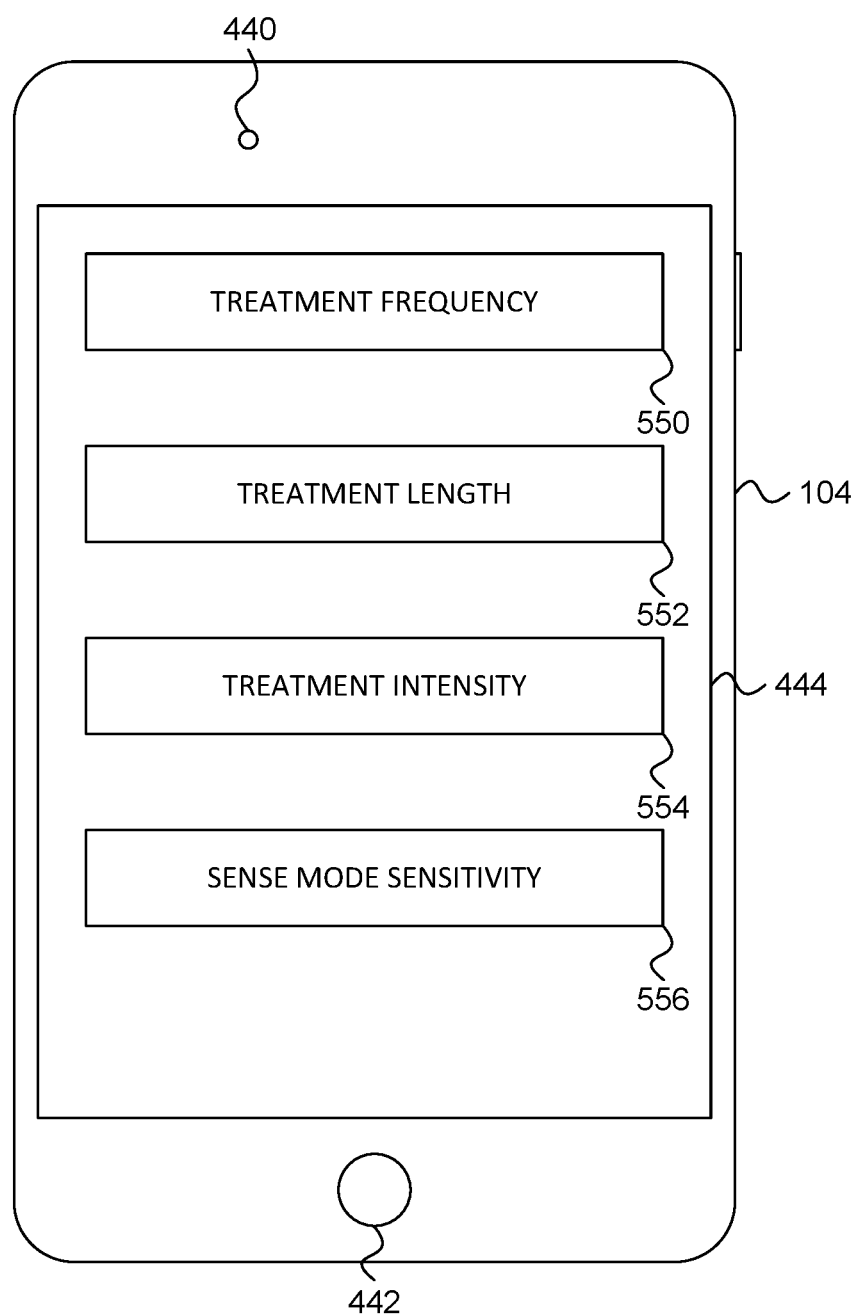
FIG. 5 is an illustration of a personal electronic device executing an aspect of a software application for controlling a handheld sinus treatment device, according to an embodiment.

FIG. 5 is an illustration of the personal electronic device 104 of FIG. 4, according to an embodiment. The personal electronic device 104 is displaying a graphical user interface that enables the user to select various icons in order to adjust settings of the handheld sinus treatment device 102. In one embodiment, the icons shown in FIG. 5 can be accessed by selecting the settings icon 448 from FIG. 4. In particular, the graphical user interface displays an icon 550 corresponding to treatment frequency, an icon 552 corresponding to treatment length, an icon 554 corresponding to treatment intensity, and an icon 556 corresponding to detect mode sensitivity.

Figure 6:
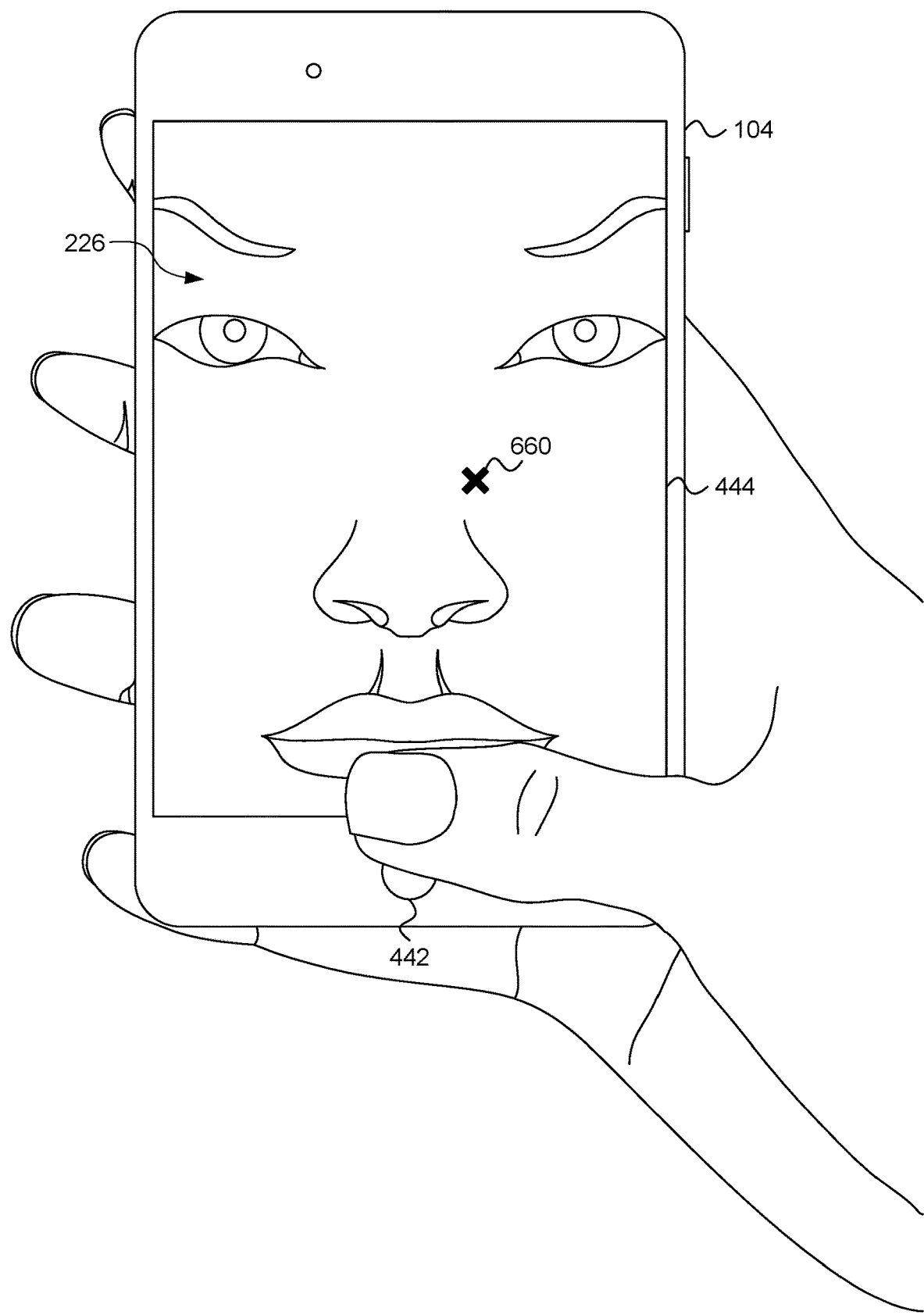
FIG. 6 is an illustration of a personal electronic device executing an aspect of a software application for controlling a handheld sinus treatment device, according to an embodiment.

FIG. 6 is an illustration of the personal electronic device 104 of FIG. 4, according to an embodiment. The personal electronic device 104 is in the treatment mode 446, as selected by the user. In the treatment mode 446, the personal electronic device 104 displays an image of the user's face 226. The image of the user's face 226 can include guidance indicators 660 that indicate the position of treatment locations 228 on the face of the user 226. The position of the treatment locations 228 can be identified during the training mode 447 described with relation to FIG. 4. As the user holds the handheld sinus treatment device 102 in one hand, the user holds the personal electronic device 104 in the other hand. The user can look at the touchscreen display 444 of the personal electronic device 104 as the user moves the treatment electrode 208 of the handheld sinus treatment device 102 on the skin of the user's face 226. The touchscreen display 444 can show both the user's face 226 and the current position of the handheld sinus treatment device 102. The user can quickly move the treatment electrode 208 to the guidance indicator 660 displayed on the touchscreen display 444. After the user has positioned the treatment electrode 208 of the handheld sinus treatment device 102 at the treatment location 228 indicated by the guidance indicator 660, the handheld sinus treatment device 102 can provide the treatment stimulation to the treatment location 228. After the user has provided the treatment stimulation to the treatment location 228 corresponding to the guidance indicator 660, the personal electronic device 104 can display a new indicator guidance 660 indicating the next treatment location 228. The user can move the handheld sinus treatment device 102 from treatment location 228 to treatment location 228 with the assistance of the guidance indicator 660 provided on the touchscreen display 444 of the personal electronic device 104 until treatment stimulation is provided to each treatment location 228.

Figure 7:
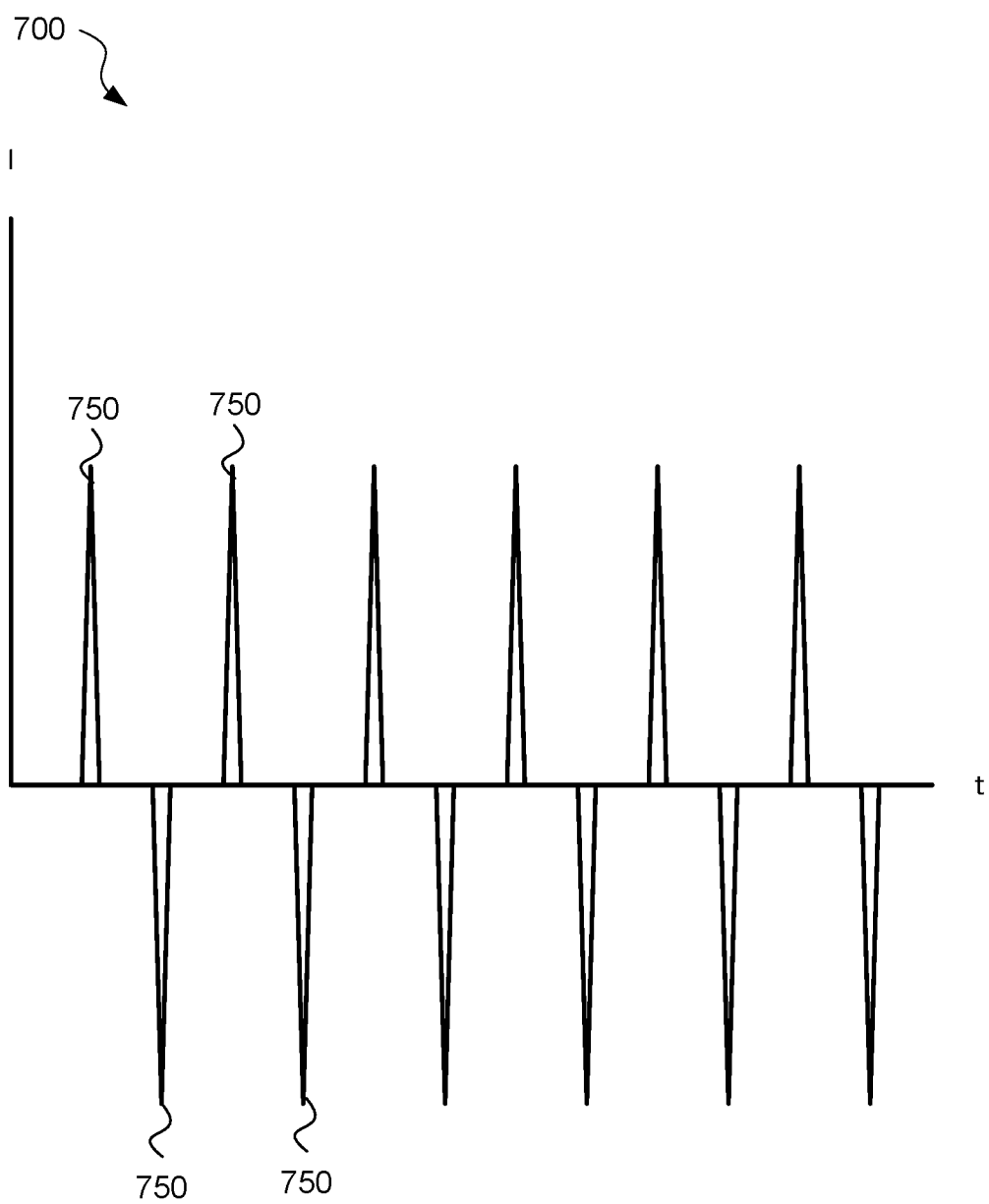
FIG. 7 is a graph of a treatment current vs time, according to an embodiment.

FIG. 7 is a graph of a treatment stimulation current (I) vs time (t), according to an embodiment. The treatment stimulation current is applied during a treatment mode of the handheld sinus treatment device 102 after the handheld sinus treatment device 102 has identified a treatment location 228. The treatment stimulation current provides relief to sinus discomfort and users.

According to an embodiment, the sinus treatment stimulation current corresponds to a series of sharp current spikes 750 or peaks. According to an embodiment, successive current spikes alternate in direction such that every other current spike flows in a first direction, while intervening current spikes flow in a second, opposite, direction.

According to an embodiment, the sinus treatment stimulation current spikes 750 correspond to the rising and falling edges of a square wave voltage signal. In one embodiment, the treatment stimulation current is generated by feeding a square wave voltage signal to a transformer via a capacitor. Those of skill in the art will recognize, in light of the present disclosure, that a treatment stimulation current in accordance with FIG. 7 can be generated in various ways. All such other ways for generating the treatment stimulation current fall within the scope of the present disclosure.

In one embodiment, the treatment stimulation current has no DC offset. The lack of a DC offset can enhance the therapeutic effect of the treatment stimulation current. This is because, in one interpretation, the rapid changes in current magnitude and direction promote physiological effects that do not occur in the presence of a DC current.

In one embodiment, the sinus treatment circuitry 329, including the microcontroller 334 and the memory 332, adjust the stimulation voltage between the conductive tip 108 and the return electrode 110 to maintain a constant treatment stimulation current during the treatment mode. In one embodiment, maintaining a constant treatment stimulation current corresponds to causing the peaks of the treatment stimulation current to have substantially the same magnitudes. In one embodiment, maintaining a constant treatment stimulation current corresponds to causing the peaks of the treatment stimulation current to have substantially the same absolute values. Thus, the positive current peaks and the negative current peaks have the same absolute value, in one embodiment. Alternatively, maintaining a constant treatment stimulation current corresponds to causing the positive current peaks to have a same first magnitude, and causing the negative current peaks to have a same second magnitude.

In one embodiment, the peaks of the sinus treatment stimulation current have a magnitude less than or equal to 1000 μA. In one embodiment, the peaks of the treatment stimulation current have a magnitude less than or equal to 600 μA. In one embodiment, the sinus treatment stimulation current spikes 750 have an average current less than or equal to 1000 μA. In one embodiment, the sinus treatment stimulation current spikes 750 have an average current less than or equal to 600 μA.

In one embodiment, the frequency of the treatment stimulation current is less than 1000 Hz. In one embodiment, the period of a single treatment stimulation current cycle corresponds to the time between current peaks of the same direction. In one embodiment, the frequency of the treatment stimulation current is between 1 Hz and 100 Hz. In one embodiment, the spikes 750 in the sinus treatment stimulation current make up less than 10% of a single cycle. In one embodiment, the spikes 750 in the sinus treatment stimulation current make up less than 5% of a single cycle. In one embodiment, the spikes 750 in the sinus treatment stimulation current make up about 3% of a single cycle.

In one embodiment, during the treatment mode, the handheld sinus treatment device 102 measures the impedance by measuring the peaks of the treatment stimulation current. In one embodiment, the handheld sinus treatment device 102 adjusts a stimulation voltage applied between the conductive tip 108 and the return electrode 110 to bring the magnitude of the peaks of the treatment stimulation current back to a desired constant value.

In one embodiment, in the detection mode in which the handheld sinus treatment device 102 identifies treatment locations, the handheld sinus treatment device 102 measures the impedance by applying a detection current with a waveform similar or identical to the treatment stimulation current waveform and measuring the magnitude of the current peaks of the detection current in order to determine the impedance. In one embodiment, the handheld sinus treatment device 102 measures the impedance by passing a detection current with a smaller magnitude than the treatment stimulation current. In one embodiment, during the detection mode, the handheld sinus treatment device 102 applies a detection voltage that is lower than the stimulation voltage applied during the treatment mode. In one embodiment, the handheld sinus treatment device 102 measures the impedance by passing a detection current with a waveform entirely different than the treatment stimulation current waveform.

Those of skill in the art will recognize, in light of the present disclosure, that in practice the treatment current may vary from the graph 700. For example, the risetime and fall time of a given sinus treatment stimulation current spike 750 may not be identical. The rise times and fall times of separate sinus treatment stimulation current spikes 750 may not be identical to each other. A given sinus treatment stimulation current spike 750 can include, at the tail end, a brief portion that flows in the opposite direction to the primary direction of the sinus treatment stimulation current spike 750. In a constant current situation, sinus treatment stimulation current spikes 750 may have slightly differing magnitudes while remaining substantially the same. There may be noise present among the current waveform. All such variations from the graph 700 fall within the scope of the present disclosure.

In one embodiment, the sinus treatment stimulation current spikes 750 are sharp increases in current followed by a sharp drop in current. In one embodiment, the rise time and fall time of a sinus treatment stimulation current spike 750 makes up 90% or more of the sinus treatment stimulation current spike 750.

Figure 8:
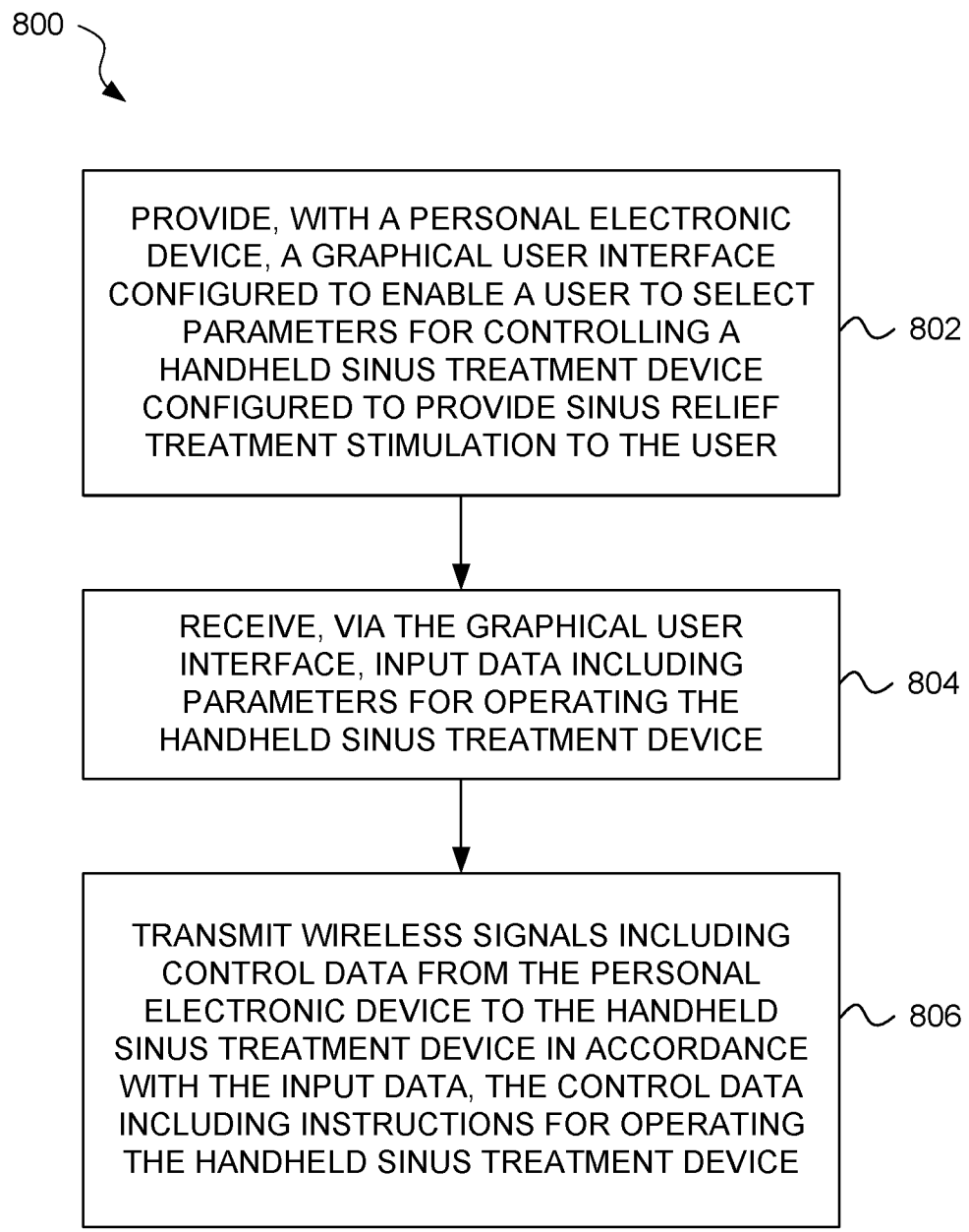
FIG. 8 is a flow diagram of a process for controlling a handheld sinus treatment device with a personal electronic device, according to an embodiment.

FIG. 8 is a flow diagram of a process 800 for operating a personal electronic device, according to an embodiment. At 802, the personal electronic device provides a graphical user interface configured to enable a user to select parameters for controlling a handheld sinus treatment device configured to provide sinus relief treatment stimulation to the user. At 804, input data is received via the graphical user interface. The input data includes parameters for operating the handheld sinus treatment device. At 806, the personal electronic device transmits wireless signals including control data to the handheld sinus treatment device in accordance with the input data. The control data includes instructions for operating the handheld sinus treatment device.

FIG. 9 is a flow diagram of a process 900 for operating a personal electronic device, according to an embodiment. At 902, a wireless receiver of a handheld sinus treatment device receives wireless signals including control data from a personal electronic device. At 904, the control data is stored in a memory of the handheld sinus treatment device. At 906, sinus relief treatment is provided to the user in accordance with the control data with a current output circuit of the handheld sinus treatment device.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A handheld sinus treatment device, comprising:
a memory;
a current output circuit including:
a treatment electrode configured to be positioned on a face of a user; and
a return electrode, wherein the current output circuit is configured to pass a stimulation current through a body of the user between the treatment electrode and the return electrode;
a wireless receiver configured to receive wireless signals including control data from a personal electronic device, wherein the control data indicates one or more parameters of the stimulation current; and
a microcontroller operably coupled to the memory, the wireless receiver, and the current output circuit and configured to receive the control data from the wireless receiver, write the control data to the memory, and cause the current output circuit to provide sinus relief treatment stimulation to the user in accordance with the control data,
wherein the current output circuit and the microcontroller are configured to cooperate to identify one or more treatment locations on the face of the user by
the microcontroller calculating and monitoring an impedance, and
identifying the one or more treatment locations by the impedance falling below a specified threshold.

2. The handheld sinus treatment device of claim 1, wherein the microcontroller is configured to control the current output circuit to provide the stimulation current to the one or more treatment locations.

3. The handheld sinus treatment device of claim 2, wherein the control data includes treatment length data specifying a time duration of the stimulation current to be applied to each treatment location.

4. The handheld sinus treatment device of claim 2, wherein the control data includes treatment strength data indicating a strength of the stimulation current to be applied to each treatment location.

5. The handheld sinus treatment device of claim 2, wherein the control data includes detection mode sensitivity data indicating a sensitivity level for identifying treatment locations.

6. The handheld sinus treatment device of claim 5, wherein the current output circuit is configured to pass a detection current through the body of the user between the treatment electrode and the return electrode.

7. The handheld sinus treatment device of claim 6, wherein the microcontroller is configured to identify the one or more treatment locations by calculating the impedance based on the detection current.

8. The handheld sinus treatment device of claim 7, wherein the control data includes impedance threshold data including the impedance threshold for identifying treatment locations.

9. The handheld sinus treatment device of claim 1, wherein the control data includes a shut down command.

10. The handheld sinus treatment device of claim 1, wherein the control data includes a power on command.

11. The handheld sinus treatment device of claim 1, wherein the wireless receiver is a radio frequency receiver.

12. The handheld sinus treatment device of claim 11, wherein the wireless receiver operates in accordance with a Bluetooth protocol.

13. The handheld sinus treatment device of claim 1, wherein the device further comprises:
a tip portion including the treatment electrode; and
a hand-contact grip portion including the return electrode.

14. The handheld sinus treatment device of claim 13, wherein the device includes a material, that is not electrically conductive, disposed between the treatment electrode and the return electrode.

15. The handheld sinus treatment device of claim 1, wherein the microcontroller, when entering into a treatment mode, maintains a constant electrical treatment stimulation current between the treatment electrode and the return electrode.

16. The handheld sinus treatment device of claim 15, wherein the microcontroller adjusts a stimulation voltage between the treatment electrode and the return electrode to maintain the constant electrical treatment stimulation current during the treatment mode.

17. The handheld sinus treatment device of claim 16, wherein the microcontroller causes peaks of the treatment electrical stimulation current to have substantially a same magnitude.

18. The handheld sinus treatment device of claim 1, wherein the microcontroller, when entering into a detection mode, calculates the impedance based on an electrical current, between the treatment electrode and the return electrode, that is maintained constant during the detection mode.

19. The handheld sinus treatment device of claim 18, wherein the microcontroller switches from the detection mode to the treatment mode based on the calculated impedance.

* * * * *